(12) United States Patent
Hall et al.

(10) Patent No.: US 6,298,257 B1
(45) Date of Patent: Oct. 2, 2001

(54) CARDIAC METHODS AND SYSTEM

(75) Inventors: Andrew F. Hall, St. Charles, MO (US); Roger N. Hastings, Maple Grove, MN (US); Walter M. Blume, Webster Groves, MO (US)

(73) Assignee: Sterotaxis, Inc., St. Louis, MO (US)

( * ) Notice: Subject to any disclaimer, the term of this patent is extended or adjusted under 35 U.S.C. 154(b) by 0 days.

(21) Appl. No.: 09/405,314

(22) Filed: Sep. 22, 1999

(51) Int. Cl.$^7$ .................................................. A61B 5/05
(52) U.S. Cl. ................................. 600/407; 600/424
(58) Field of Search ........................... 600/424, 427, 600/407, 429, 374, 9, 11, 12, 13, 509, 114, 117; 606/130, 108; 128/899; 604/95, 891.1; 361/141, 143, 146

(56) References Cited

U.S. PATENT DOCUMENTS

| | | | |
|---|---|---|---|
| 4,869,247 | * | 9/1989 | Howard et al. ............... 128/303.1 |
| 6,014,580 | * | 1/2000 | Blume et al. .................. 600/424 |
| 6,015,414 | * | 1/2000 | Werp et al. ................... 606/108 |
| 6,173,199 | * | 1/2001 | Gabriel ......................... 600/424 |

\* cited by examiner

*Primary Examiner*—Marvin M. Lateef
*Assistant Examiner*—Eleni Mantis Mercader
(74) *Attorney, Agent, or Firm*—Harness, Dickey & Pierce, P.L.C.

(57) ABSTRACT

A method of applying a magnetic medical device to the surface of an internal body structure, the medical device having a magnetically responsive element associated with its distal end, the method comprising applying a magnetic field to the distal end of the magnetic medical device to apply a measured and controlled force between the medical device and tissue to facilitate cardiac sensing, mapping, pacing, ablation, biopsying and other procedures. Contact is confirmed by the angle between the direction of the magnetic medical device and the applied magnetic field, and the contact force is controlled by controlling at least one of the magnetic field direction and the magnetic field strength.

40 Claims, 5 Drawing Sheets

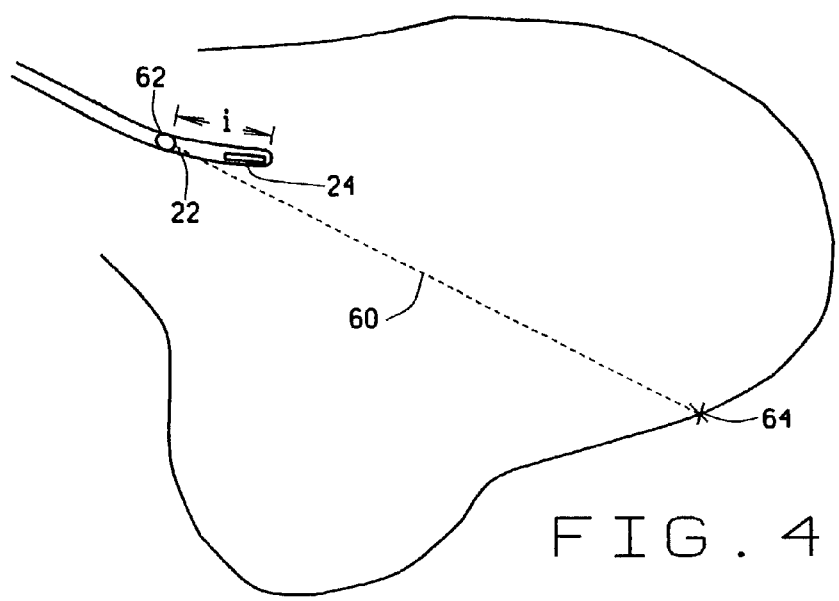
FIG. 4
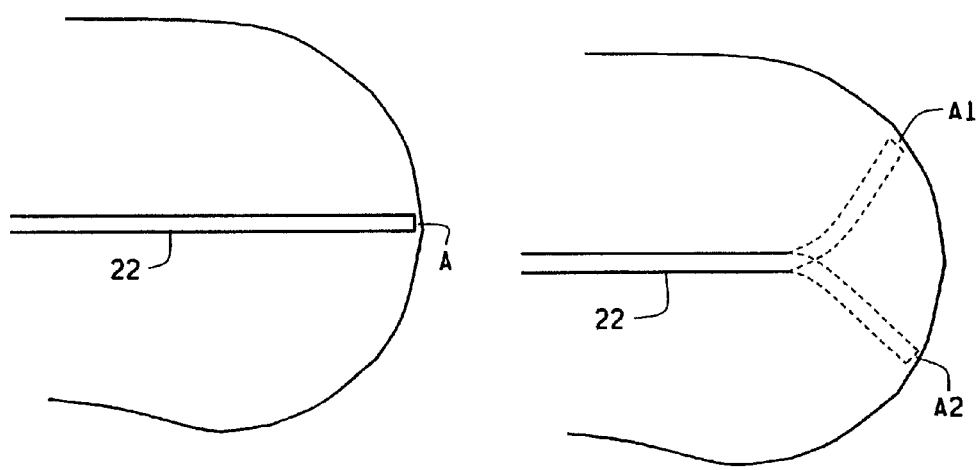
FIG. 5A
FIG. 5B
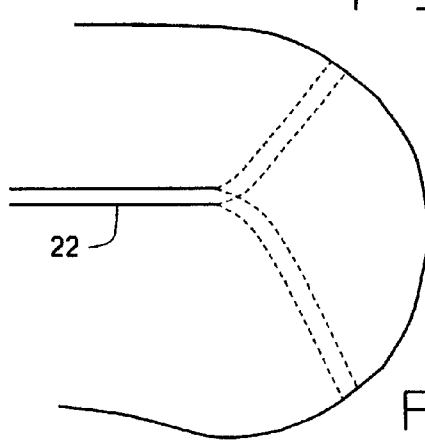
FIG. 5C

CARDIAC METHODS AND SYSTEM

FIELD OF THE INVENTION

This invention relates to cardiac procedures, and in particular to magnetically assisted methods for conducting cardiac procedures, and a system for conducting cardiac procedures.

BACKGROUND OF THE INVENTION

Many cardiac procedures employ catheters and other similar devices that are manipulated into the chambers of the heart. Electrophysiology (EP) is a discipline in which catheters are fed into the open chambers of the heart, generally gaining access via the great veins. The distal section of the catheter is manually manipulated within the heart by tactile control of the proximal catheter section, which can be up to four feet or more from the distal section, often in the groin area of the patient. Precise manipulation of the catheters is desired to record the electrical signals emanating from the endocardial surfaces. It is desirable to drag the catheters along curved paths, maintaining contact with the inside or endocardial surface of the heart chambers, even as the heart muscle constricts and relaxes. It is further most desirable to identify the anatomical features of the heart which are in contact with the catheter, and to record their location in space. It is then often desirable to return to a specific location to either re-record the electrical signal or to apply energy through the catheter to ablate tissue which is involved in the generation of abnormal electrical signals or arrhythmias.

Precise manipulation of the distal end of recording and ablation catheters from the proximal end is generally difficult and often impossible because of the squeezing motions of the heart, the convoluted anatomy of the heart chambers (especially when the catheter must pass through one chamber to access an adjacent chamber), and the presence of anatomical structures such as cords and tribiculae.

The catheters presently used for these procedures are usually navigated using a mechanically navigated guide wire, or are themselves directly mechanically navigated. These mechanically navigable catheters are difficult to accurately control, and become increasingly so as the catheter twists and turns. One difficulty with presently available cardiac catheters is that it is difficult to determine when the catheter is in contact with the surface of the heart. Moreover, even when the catheter is in contact with the surface of the heart, it is not possible to determine the contact pressure.

SUMMARY OF THE INVENTION

The present invention relates to an improved method of and system for navigating catheters within the heart and surrounding blood vessels, employing an externally applied magnetic field. This not only facilitates navigation within the heart and blood vessels, but also allows the catheter to contact the surface of the heart with certainty, and even with a controllable predetermined force. Through the use of localization techniques, such as magnetic localization or RF localization, the catheter can be precisely located in the body to thereby locate the point where the catheter is touching, for structural and physiological mapping, and to facilitate returning the catheter to a previously identified site. Moreover by providing the appropriate control of the magnetic field generating device and advancement of the catheter, the catheter can be automatically navigated to respected points on the surface of the heart for diagnostic or treatment purposes. The catheter can also be automatically navigated to a plurality of points for structural and/or physiological mapping.

Broadly, magnetically controlled EP catheters are disclosed in pending utility patent application Ser. No. 09/151,615, filed Sept. 11, 1998, entitled "Magnetically Navigable Telescoping Catheter And Method Of Navigating Telescoping Catheter", and pending U.S. patent application Ser. No. 09/311,686 filed May 13, 1999, entitled "Magnetic Medical Device and Method of Navigating Magnetic Medical Devices with Magnetic Fields and Gradients" incorporated herein by reference. The present invention is directed to systems that control intracardiac catheters, and features of such systems which are unique to the field of cardiology.

Perhaps the simplest implementation of a system for navigating magnetic catheters over the endocardial surfaces involves bi-planer fluoroscopic imaging of the catheter, and point-and-click direction of the catheter tip, as described in U.S. patent application Ser. No. 09/020,798, filed Feb. 9, 1998, entitled "Device and Method for Specifying Magnetic Field for Surgical Applications" in the context of endovascular navigation. The physician uses a joystick to specify the location of the catheter tip and desired direction of motion on each of the two bi-planer images. The present invention improves upon this by providing a method and system that not only permits navigation, but provides the ability to positively contact the surface, and do so with a specified force, or at least a force between specified minimum and maximum values. This is important for insuring that that procedures employing the catheter are properly carried out.

A second aspect of the invention is the coupling of localization of the distal end of the medical device with the magnetic navigation to provide information for automation of the navigation of the medical device. This allows the physician to specify a point on the bi-plane images that he desires the catheter tip to touch, and the computer generates the necessary magnet commands via the known catheter tip location and the desired or specified location. This becomes useful in electrophysiology because in addition to automatically positioning the medical device where the physician specifies, the system positively contacts the device with the surface of the heart, and can do so with a specified force. There are many possibilities for locating the catheter tip, including the use of beams of electromagnetic or ultrasound energy in addition to the X-ray beams. Methods for using the magnetic surgery source fields for localization have been disclosed U.S. utility patent application Ser. No. 09/020,942, filed Feb. 9, 1998, entitled "Method and Device for Locating Magnetic Implant by Source Field", as have the use of AC magnetic fields as disclosed in U.S. Pat. No. 4,173,228, for Catheter Locating Device, both of which are incorporated herein by reference. Other suitable localization methods and apparatus are disclosed in U.S. Pat. No. 5,752,513, issued May 19, 1998, for "Method and Apparatus for Determining Position of Object"; U.S. Pat. No. 5,729,129, issued Mar. 17, 1998, for "Magnetic Location System with Feedback Adjustment of Magnetic Field Generator"; U.S. Pat. No. 5,558,091, issued Sep. 24, 1996, for "Magnetic Determination of Position and Orientation"; and U.S. Pat. No. 5,833,608, issued Nov. 10, 1998, for "Magnetic Determination of Position and Orientation", each of which is incorporated herein by reference.

According to a third aspect of this invention preoperative images of the heart are made and used in the navigation. The use of preoperative images for magnetic navigation is disclosed in U.S. Pat. No. 4,869,247, issued Sep. 26, 1989, entitled "Video Tumor Fighting System" and in U.S. Pat. No. 5,125,888, issued on Jun. 30, 1992, entitled "Magnetic Stereotactic System for Treatment Delivery", incorporated herein by reference. According to the present invention, a pre-operative image, for example an MRI or CT image, is taken with a reference catheter in place, or using an anatomical feature such as a rib or the sternum as a reference marker. A dynamic, i.e., moving pre-operative image of the heart can then be displayed during the procedure, with the heart motions referenced to the ECG signal to properly align the motion with the patient's cardiac cycle. The reference features are continuously localized via bi-planer image processing or localization sensors to place the pre-operative image in proper perspective, and allow correct visualization of the catheters on the image. With all catheters localized in space, the pre-operative image can be rotated to desired imaging angles, showing the catheters in proper perspective on the image as well. The physician points and clicks on the image to anatomical spots that the physician would like to access with the catheter tip, and the computer commands the magnetic fields and an advancement mechanism to accurately move the catheter tip to the target location. A motion control algorithm which incorporates feedback of the current catheter location is generally used to precisely control the catheter. Of course, more complex physician interfaces are possible. For example, the physician may specify an array of points at which he wishes to record electrograms or ablate in sequence, and the MSS can automatically carry out the commands.

The cardiac electrophysiological methods and system of the present invention provides several advantages in navigation in the heart chambers. Present EP procedures often take several hours, due in part to the difficulties associated with mechanical navigation of catheters. While the method and system of the present invention can reduce manual navigation time, they also make possible automated navigation, in which the physician can remain out of the X-ray field, and command the catheters remotely. The catheters can be automatically advanced and withdrawn by a computer controlled mechanism, while being steered by computer controlled magnetic fields (although the fields can be set up to provide advancement forces as well). Reduced physician X-ray exposure is an important consideration, as is operation by expert physicians located at remote sites around the world.

A current serious problem with both mapping and ablation using mechanically manipulated catheters is the loss of contact between the catheter tip and the tissue during part of the cardiac cycle. For example, the heart wall may move away from a catheter tip which is held in a fixed position during the filling portion of the heart cycle, making contact again as the heart tissue contracts. Variable contact can cause noisy ECG recordings, and can cause coagulation of blood on an ablation electrode, or result in incomplete or inadequate ablation of the tissue. With the method and system of the present invention, the catheter tip is mechanically only weakly coupled to the proximal catheter body, so that the magnetic force controls the tissue contact. The magnetic force is uniform in strength and direction over the volume of the heart, so the catheter tip moves with the motion of the heart, remaining in contact with tissue throughout the cardiac cycle.

The method and system of the present invention can also provide an important measure of safety to the patient. Mechanical manipulation of catheters which have a variable resistance to movement along their length can lead to excessive forces accidentally being applied against tissue. This can cause perforation of the heart wall, which is often catastrophic. This is eliminated with the present method and system where contact with the surface, and the force of the contact with the surface can be monitored and controlled.

These and other features and advantages will be in part apparent and in part pointed out hereinafter.

BRIEF DESCRIPTION OF THE DRAWINGS

FIG. 4 is an illustration of the chamber of the heart, showing a simple navigation algorithm that can be implemented by the system to guide the distal end of a catheter to a point of the surface of the heart identified by the physician;

FIG. 5A is an illustration of a heart chamber, showing a catheter navigated to contact the wall of the chamber;

FIG. 5B is an illustration of the heart chamber with the catheter retracted slightly, and showing in phantom two of the positions of the distal end of the catheter in mapping the chamber;

FIG. 5C is an illustration of the heart chamber with the catheter retracted further, and showing in phantom two of the positions of the distal end of the catheter in mapping the chamber;

Corresponding reference numerals indicate corresponding parts throughout the several views of the drawings.

DETAILED DESCRIPTION OF THE INVENTION

Figure 1:
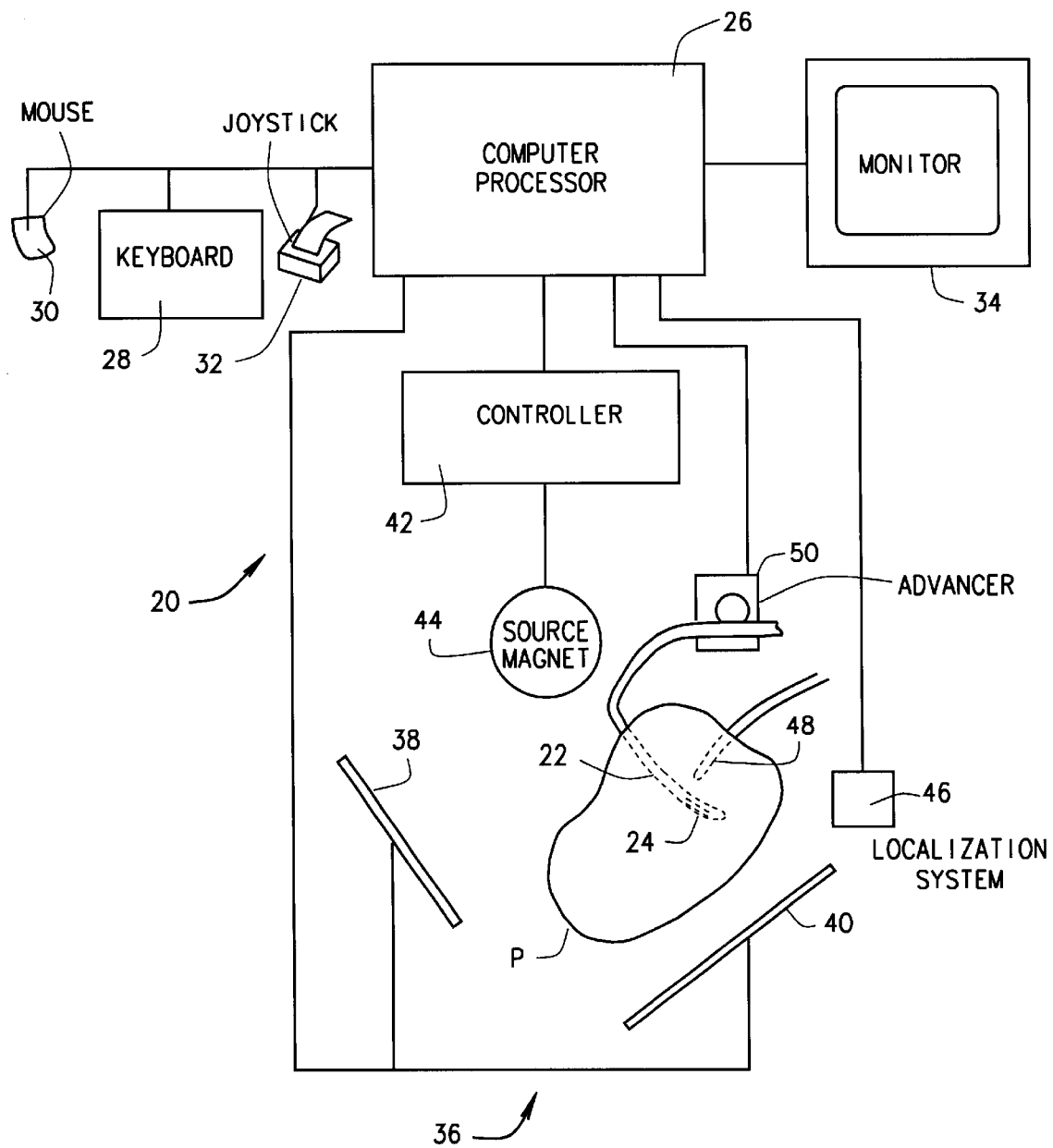
FIG. 1 is a schematic view of a system for conducting magnetically assisted cardiac electrophysiology procedures in accordance with this invention.

A system for conducting magnetically assisted cardiac electrophysiology procedures in accordance with this invention is indicated generally as 20 in FIG. 1. The system 20 comprises a magnetic medical device, such as an electrophysiology catheter 22 having a magnetically responsive element 24 associated with its distal end, which is disposed in a patient's heart P.

While this description references electrophysiology catheter 22, the invention is not so limited and can apply to any elongate medical device, including other types of catheters, endoscopes, guide wires, and other elongate medical devices. The magnet element 24 associated with the distal end of the catheter 22 can be one or more permanent or permeable magnetic bodies, responsive an applied magnet field. In the preferred embodiment the magnet element 24 is a permanent magnet body made, for example from neodymium-iron-boron, whose magnet direction is aligned with the axis of the catheter 22.

The system further comprises a computer processor 26, which has one or more standard input devices, such as keyboard 28, mouse 30, and joystick 32. A display 34, connected to the processor, is provided to allow the physician to view the procedure, and facilitate the input of instructions. In accordance with the preferred embodiment, the system includes an imaging system for imaging in the operating region of the patient. This imaging system could be a bi-planar fluoroscopic system 36, having first and second imaging plates 38 and 40. The imaging system is connected to the computer processor, and the resulting images are processed, and displayed on display 34.

The computer processor 26 is connected to a controller 42 for controlling the magnetic field and direction applied by an external source magnet 44 in the operating region. The source magnet 44 may be, for example a stationary magnet or set of magnets that project a magnetic field into the operating region such as the system disclosed in U.S. Pat. No. 5,125,888, issued on Jun. 30, 1992, for "Magnetic Stereotactic System for Treatment Delivery", incorporated herein by reference, or more preferably the system disclosed in U.S. utility patent application Ser. No. 09/211,723, filed Dec. 14, 1998, for "Open Field System for Magnetic Surgery" incorporated herein by reference. Alternatively, the magnet could be a moveable magnet that is articulated to change the field direction and/or field strength, such as the magnet disclosed in U.S. patent application Ser. No. 09/189, 633, filed Nov. 10, 1998, for Articulated Magnetic Guidance System, incorporated herein by reference. Thus, where the source magnet 44 is a set of magnet coils the controller 42 may simply be a control for changing the currents in the set of magnets, and where the source magnet 44 is a single permanent magnet or electromagnet, the controller 42 may be an articulation mechanism for translating and rotating the magnet.

The system 20 preferably also includes a location device 46 that is locating the catheter 22 and preferably also a reference catheter 48 in three dimensional space. With data from the location system the relative position of the catheter 22 to the reference catheter 48 can be determined. This allows the position of the catheter 22 to be registered with, and displayed against, a preoperative image made with the reference catheter 48 in place. A variety of location systems can be used, for example ultrasonic, magnetic, or RF location systems. The image processing associated with the bi-planar fluoroscopic imaging equipment can also be used to localize the catheter 22 if necessary.

Finally the system 20 includes a device 50 for advancing and retracting the catheter 22 under the control of the computer processor 26.

The catheter 20 is magnetically navigated to and through the heart through the application of an external magnetic field from the source magnet 44, which aligns the magnet element 22, and thus the distal end of the catheter 22, with the magnetic field. By selectively aligning the distal end of catheter, and advancing the catheter, the catheter can be quickly and easily navigating to any point within the heart. However, more importantly, in accordance with the principles of this invention, and unlike the prior art, the catheter 20 can be navigated into positive contact with the surface of the heart. Through the localization system 46, such as a magnetic, ultrasonic, or RF localization, the direction of the distal end of the catheter 20 can be determined. When the distal end of the catheter 22 is in contact with the surface of the heart the distal end portion turns at greater than usual angle with respect to the applied magnetic field. Thus contact with the surface of the heart can be detected by monitoring the angle between the direction of the distal end of the catheter and the direction of the applied magnetic field.

Figure 2A:
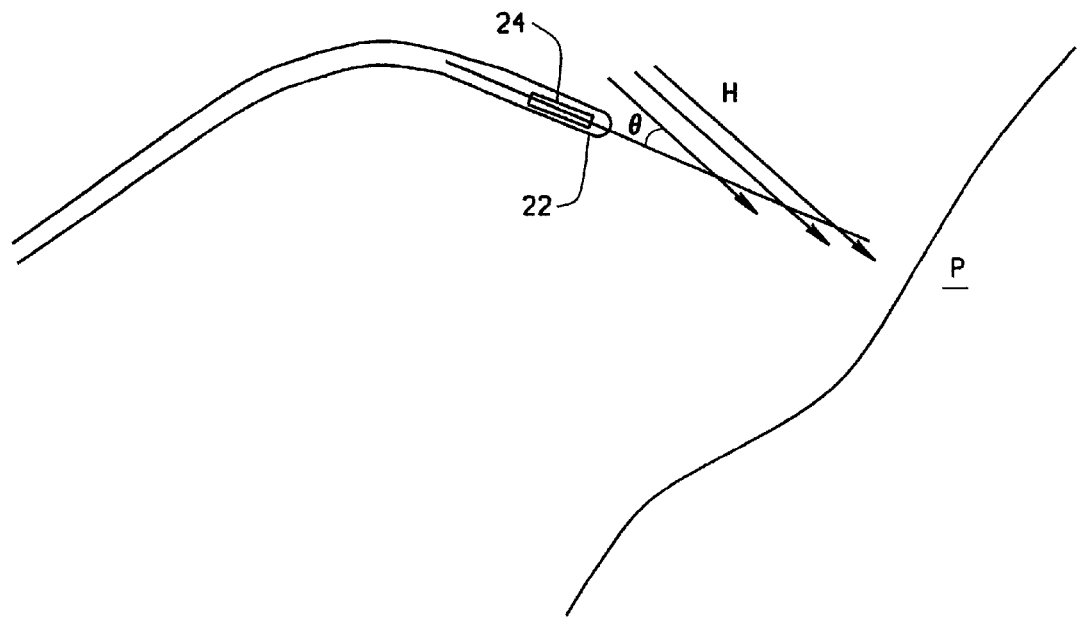
FIG. 2A is an illustration of the distal end of a catheter inside the chamber of a heart, as it is being advanced into contact with the wall of the heart.
Figure 2B:
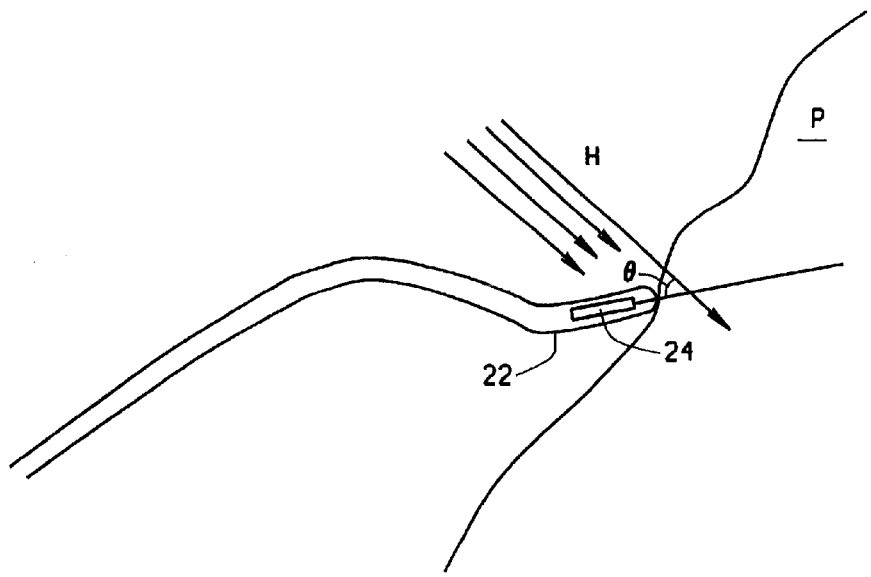
FIG. 2B is an illustration of the distal end of the catheter inside the chamber of the heart, after it has been advanced into contact with the wall of the heart.

As shown in FIG. 2A, due to the stiffness and other physical properties of the catheter 20, the distal end of the catheter does not precisely align with the direction of the applied magnetic field, and there is typically some characteristic lag angle between the distal end of the catheter 20 and the direction of the applied magnetic field H. However, as shown in FIG. 2B, when the distal end of the catheter 20 is in contact with the surface of the heart, the difference between the angle of the catheter and the angle of the applied magnetic field becomes even greater, and thus contact with the surface can be determined and confirmed by measuring this angle. Thus, the catheter is navigated into contact with the heart tissue at a particular point, advancing until the difference between the direction of the distal end of the catheter and the applied magnetic field exceeds a predetermined amount. This predetermined amount preferably takes into account the lag angle characteristic of the catheter.

Once contact with the surface of the heart is confirmed, through various localization techniques, the location of the contact point can be determined. This positional data can be stored for future use. Because the surfaces of the heart moves, due to both the internal beating of the heart, and the external shifting of the heart with respiration and other body movement, the positional data can be coordinated with timing data. For example, in a mapping procedure, the positional data collection can be coordinated with the patient's ECG, so that the data is acquired from a number of different locations at the same point in the heart cycle to allow construction of a map of the heart at a selected point in the heart cycle. Alternatively, positional data points can be collected at several points in the cardiac cycle to allow construction of maps (including three-dimensional displays) at different points in the cardiac cycle or a dynamic map showing motion during the cardiac cycle.

Because the heart moves, it is possible that during the cardiac cycle the heart moves out of contact with the distal end of the catheter 22. This can be detected by measuring or monitoring the angle between the direction of the distal end of the magnetic medical device and direction of the applied magnetic field. If during the cardiac cycle this angle approaches zero, or at least the characteristic lag angle, then it is possible that the heart does move out of contact with the catheter. This can be corrected by advancing the catheter, or by changing the direction of the applied magnetic field.

Many cardiac procedures, such as mapping, pacing, and ablation, require good contact between the catheter and the wall of the heart. Thus it is not enough to know that the catheter is in contact with the heart, but it is desirable to know that the catheter is contacting the heart with at least a certain minimum force. In accordance with this invention, it is possible to determine the force between the distal end of the magnetic medical device and the surface of the heart. This force is a function of the magnetic moment of the magnetic body 24, and the direction and field strength of the applied magnetic field.

Figure 3A:
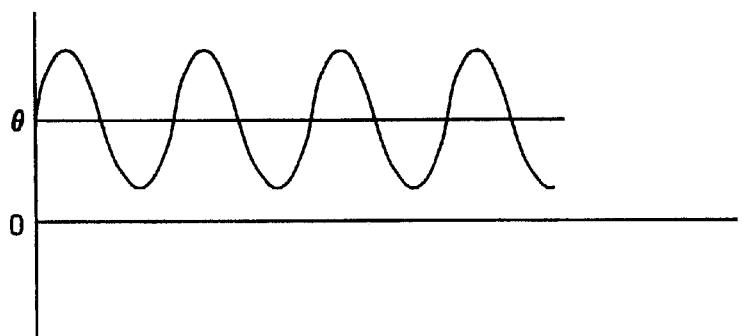
FIG. 3A is an plot of the angle between the direction of the distal end of the catheter and the direction of the applied magnetic field in contact with the heart wall during the normal cycle of the heart.
Figure 3B:
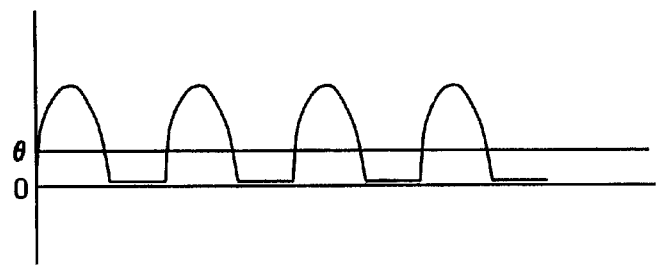
FIG. 3B is a plot of the angle between the direction of the distal end of the catheter and the direction of the applied magnetic field in contact with the heart wall during only a portion of the normal cycle of the heart.
Figure 3C:
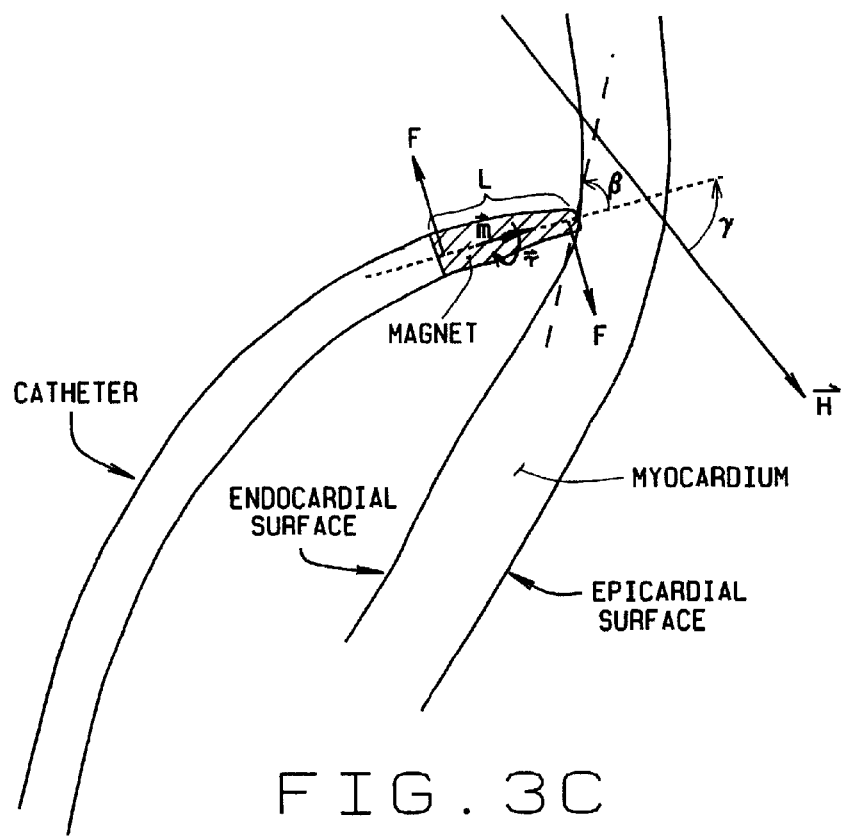
FIG. 3C is an illustration of the contact between the distal end of the catheter and the surface of the heart.

As illustrated in FIG. 3C, the distal end of the catheter 22 is pressed against the surface of the heart by the application of an external magnetic field H, whose magnitude is under direct control of the physician. The torque on the magnet element, which is applied at its center, is given by:

$$\tau = m \times H \quad (1)$$

or in terms of magnitudes:

$$\tau = m \times H \times \sin(\gamma), \quad (2)$$

where $\tau$ is the torque trying to align the magnet with the applied magnetic field, m is the magnetic moment of the magnet, a known quantity which can be measured precisely, H is the magnetic field magnitude which is under control of the physician, and $\gamma$ is the angle between the axis of the magnet and the applied magnetic field. The magnetic field direction is known and controlled by the physician, while the orientation of the magnet is determined by fluoroscopic imaging or the output of a localization sensor located in the proximity of the magnet element 24. Thus, the angle $\gamma$ is a known quantity, and the torque is accurately computed from Eq. (2).

The magnetic force applied to the magnet is the couple which creates the alignment torque, as shown in FIG. 3C. This force is given in terms of the length L of the magnetic element, L, and Eq(2) by:

$$F = mH\sin(\gamma)/L \quad (3)$$

This force can be resolved into components parallel and perpendicular to the tissue. If the angle that the catheter tip makes with the tissue, $\beta$, is determined via the anatomical imaging of the tissue, the component of force normal to the tissue plane is given by:

$$F = mH\sin(\gamma)\cos(\beta)/L \quad (4)$$

Finally, the catheter itself exerts a restoring force in the magnet which reduces the net force applied to the tissue. This restoring force will depend upon the physical properties of the catheter and the curvature of its distal section. The restoring force can be measured in the lab and tabulated in look up tables, or parametertized in a formula to determine the net tissue force.

Since the restoring force resists the magnetic tissue force, it can be said with confidence that Eq. (4) represents an upper bound on the tissue force, which will apply when the catheter makes a floppy connection proximal to the magnet. If the angle between the catheter tip and the tissue is unknown because of inadequate tissue imaging, Eq. (3) will represent an upper bound on the tissue force, since the cosine in Eq. (4) is bounded by unity. Finally, if the angle between the catheter tip and the magnetic field is unknown due to lack of localization/orientation data, F=mH/L represents an upper bound on the tissue force, since the sine is bounded by unity.

An absolute upper bound on the magnetic force applied to the tissue by the catheter tip is given by the equation F=mH/L. This will represent an absolute upper bound on the tissue force providing that the distal section of the catheter is manipulated magnetically and not mechanically. If the orientation of the catheter tip is known relative to the applied field, Eq. (3) represents an improved upper bound on the force that the catheter exerts on the tissue. If the angle between the catheter tip and the tissue plane is known, Eq. (4) represents an even more accurate upper bound on the force exerted normal to the tissue. Finally, catheter material restoring forces can be measured in the lab and stored in the computer to give an accurate value of the tissue force when all variables are known. The tissue force or its upper bound can be displayed, for example in grams of force, on the physician display. The physician can avoid predetermined bounds on the force, or the system can automatically limit the force to values known to prevent perforation of the heart wall.

The above discussion assumes that a magnetic field which is spatially uniform is applied to the magnetic tipped medical device or agent. In this case a torque is exerted on the distal magnet which attempts to align the it with the direction of the applied magnetic field. If an external field is applied which is not spatially uniform, a second type of force will be exerted on the distal magnet, pulling it in the direction of stronger external magnetic field. The gradient field may also be controlled in both magnitude and direction to exert known forces on the medical device. It may be measured accurately by knowing the components of the field gradients being applied, knowing the magnetic moment of the distal magnet, and knowing the orientation of the distal magnet relative to an external coordinate system.

Given a Cartesian coordinate system fixed in the laboratory, the gradient force acting on a small magnet of magnetic moment "m" is given by:

$$F = (m \cdot \nabla) H \quad (5)$$

where F is the gradient force vector, H is the applied magnetic field vector, and $\nabla$ is the "del" operator. If the orientation of the moment vector is known (via bi-planer fluoroscopy, localization sensor, or other means) then its Cartesian components are also known. In terms of Cartesian components, Eq. (5) becomes:

$$F_x = m_x \frac{\partial H_x}{\partial x} + m_y \frac{\partial H_x}{\partial y} + m_z \frac{\partial H_x}{\partial z} \quad (6)$$

$$F_y = m_x \frac{\partial H_y}{\partial x} + m_y \frac{\partial H_y}{\partial y} + m_z \frac{\partial H_y}{\partial z}$$

$$F_z = m_x \frac{\partial H_z}{\partial x} + m_y \frac{\partial H_z}{\partial y} + m_z \frac{\partial H_z}{\partial z}$$

Equation (6) allows quantitative computation of the gradient force in MKS units. For gradients created with a single external magnet, the gradient force pulls generally in the direction of this source magnet.

Thus the force of contact between the distal end of the catheter 22 and surface of the heart can be determined. Because the magnetic moment of the magnetic element 24 is constant, so long as the magnetic field strength is held reasonably constant, the force applied by the catheter 20 is a function of the angle between the direction of the distal end of the catheter and the direction of the applied magnetic field. This angle is preferably monitored to ensure that the catheter remains in contact with the surface of the heart, and is also representative of the force. Thus the force can be controlled by controlling the field direction within the heart. Alternatively, the force the catheter applies to the surface of the heart can be increased by increasing the magnetic field. This can be adapted to maintain a minimum force against a moving surface, such as the heart by ensuring that the field strength and angle between the distal end of the catheter and the direction of the applied magnetic field are such as to maintain a preselected minimum force during the entire cardiac cycle. Alternatively, the use of the catheter for example in make electrophysiology measurements of the heart or applying energy for tissue ablation, can be timed with the cardiac cycle so that measurements are made or the ablation energy is applied when the force between the catheter and the surface exceeds a predetermined minimum.

The ability to measure and control the force between the catheter and the surface also permits the maximum force to be controlled, The force applied by the distal end of the catheter can be measured, and reduced by reducing the strength of the applied magnetic field, or changing the direction of the applied magnet field.

The combination of the ability to control the direction of the distal end of the catheter, to automatically advance the catheter, to detect when the catheter is in contact with the surface of the heart, and to locate the digital end of the catheter in space, permits the catheter to be automatically navigated to one or more selected points, to one or more points in a predetermined pattern, or to one or more points in that are dynamically determined.

A convenient way of implementing automated navigation of the catheter 22 utilizes a preoperative image. A reference catheter 48 is navigated into the coronary sinus. This reference catheter 48 may be a standard EP mapping catheter which has a localization element at its distal tip. A preoperative image is made of the heart, for example using CT or MRI. The reference catheter 48 allows subsequent real time images of the catheter 22 to be coordinated with the preoperative image of the heart. A localization system, such as a bi-planer fluoroscopy visualization system, an AC electromagnetic field system, an ultrasound system, or an RF system can be used to determine the position and the orientation of the reference catheter 48 in a fixed reference frame of reference. The localization system can also be used to determine the position and orientation of the catheter 22 in the same fixed frame of reference. The relative positions and orientations of the catheter 22 and the reference catheter 48 can be mathematically determined, and the location and orientation of the catheter 22 registered with and displayed on the preoperative image.

The physician can either pre-plan a path for the catheter, or control the device in real time by passing commands to external source magnets which guide and/or control the device within the body via magnetic coupling to magnets imbedded within the distal portion of said devices. The physician control of the magnets is preferably accomplished via an intuitive interface (joy stick, touch pad, mouse or other) which allows the physician to directly and visually manipulate the medical device while a computer interprets the physician's commands and provides the necessary changes in the currents in the external magnets or position of external magnets.

With a point and click interface, the physician uses a joystick or mouse to move a cursor or indicator over the preoperative image, identifying a location on the preoperative image by operating the trigger on the joystick or clicking the mouse. The processor can control the magnetic field generating apparatus and the catheter advancing mechanism to advance the distal end of the catheter toward the selected point, according to a predetermined navigation algorithm. For example as shown in FIG, 4, the algorithm call plot a straight-line path 60 from the starting position 62 of the catheter 22 to the selected point 64. The processor 226 then determines the difference between the actual position of the catheter and the straight-line path 60, adjusts the magnetic field direction, and incrementally advances the catheter, a distance i. The processor 26 repeats this process of determining the position of the distal end of the catheter 22, determining the variance between the actual position of the distal end of the catheter and the planned path 60, adjusting the direction of the applied magnetic field, and advancing the catheter until the distal end of the catheter contacts the surface at the selected point 64. The contact between the distal end of the catheter and the surface can be detected by the variation between the direction of the distal end and the direction of the applied magnetic field, as described above. The method and system of the present invention can be employed for ablating tissues and other arrhythmia treatment methods and apparatus, such as those disclosed is U.S. Pat. No. 5,840,025, issued Nov. 24, 1998, for "Apparatus and Method for Treating Cardiac Arrhythmias"; U.S. Pat. No. 5,443,489, issued Aug. 22, 1995, for "Apparatus and Method for Ablation"; U.S. Pat. No. 5,718, 241, issued Feb. 17, 1998, for "Apparatus and Method for Treating Cardiac Arrhythmias with No Discrete Target"; U.S. Pat. No. 5,480,422, issued Jan. 2, 1996, for "Apparatus for Treating Cardiac Arrhythmias"; and U.S. Pat. No. 5,391, 199, issued Feb. 21, 1995, for "Apparatus and Method for Treating Cardiac Arrhythmias"; each of which is incorporated herein by reference.

Of course rather than identify a single point, the physician can use the interface to identify a series of points in a path For the catheter 22 to follows, and thereby quickly, easily, and automatically direct the catheter into a particular chamber of the heart. After the distal end of the catheter enters the selected chamber of the heart, it may be directed to contact selected points of interest for mapping the structure or electrophysiology of selected portions of the chamber, for pacing; for selectively ablating tissue, for targeted delivery of diagnostic or therapeutic agents, or for placing medical devices, such as pacemaker leads.

Figure 6:
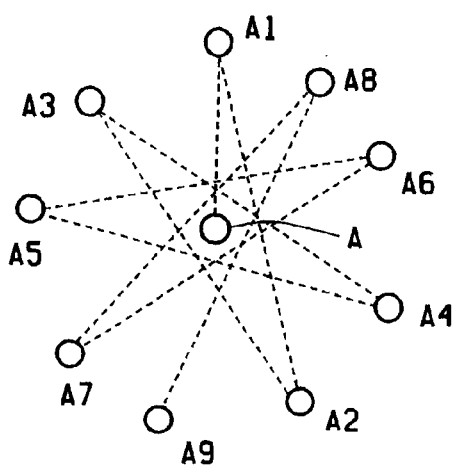
FIG. 6 is an illustration of a possible automated mapping pattern that could be implemented by the computer processor controlling the navigation of the catheter.

The ability to automatically navigate allows automated mapping. The processor can be programmed to automatically move the distal end of the magnetic medical device according to a predetermined pattern. For example, as shown in FIG. 5A, the distal end of the catheter is navigated to contact a point A on a chamber of the heart. Thereafter, the processor automatically navigates the distal end of the catheter to map the stricture. As shown in FIG. 5B, the catheter 22 is retracted slightly, and the distal end of the catheter is magnetically navigated radially outwardly until it contacts the surface of the heart, when contact is detected, then the position is determined, and the catheter is moved nearly diametrically across until it contacts the surface of the heart. When contact is detected, the position is determined, and this process is continued until a set of points surrounding the origin are contacted. The precise localization of this set of points defines the geometry of the endocardial surface of the heart chamber. Such a set of successive contacts from point A to $A_1$ to $A_9$ is shown in FIG. 6. As shown in FIG. 5C, the catheter 22 is again retracted and the above process is repeated.

Of course in making a structural map of the surface of the heart, a physiological map can also be made. Thus while taking positional data, some physiological property at the location can be measured, for example the electrical signal, electrical potential, temperature, chemical activity, or other property can be sensed. This property can be measured, and a map of the property can be made.

Rather than mapping particular points, the catheter can be dragged in lines along the surface of the heart, while periodically or continuously determining the position of distal end of the catheter. By repeating this process at several different angular orientations, a "wire-frame" map of the chamber can be constructed.

Figure 7:
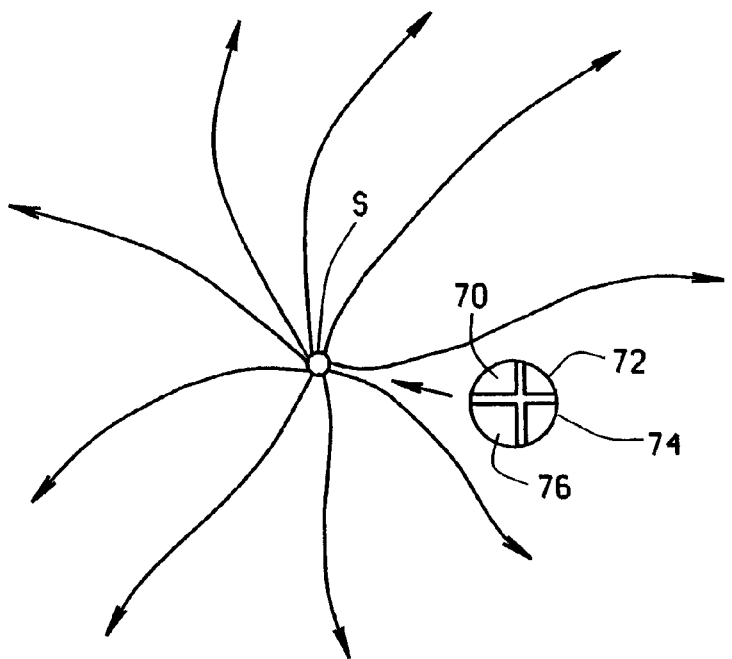
FIG. 7 is a schematic view of a signal direction find catheter that can be used with an automated control for finding the source of an electrical signal on the surface of the heart.

The automatic navigation feature allows the mapping to proceed dynamically. For example as shown in FIG. 7, the end of the catheter 22 can be provided with a directional electrodes 70, 72, 74, and 76, that can measure a direction of increasing potential. by processing the signals measured by each of the electrodes, a signal direction can be obtain. The measured signal could thus be used to direct the subsequent navigation to automatically converge upon the source S of the signal. This is particularly helpful in locating the focus of the arrhythmia.

The system and method of the present invention facilitate other mapping procedures, such as those disclosed in U.S. Pat. No. 5,738,096, issued Apr. 14, 1998, for "Cardiac Electromechanics", U.S. Pat. No. 5,568,809, issued Oct. 29, 1996, for "Apparatus and Method for Intrabody Mapping"; U.S. Pat. No. 5,713,946, issued Feb. 3, 1998, for "Apparatus for Intrabody Mapping"; U.S. Pat. No. 5,546,951, issued Aug. 20, 1996, for "Method and Apparatus for Studying cardiac Arrhythmias"; U.S. Pat. No. 5,694,945, issued Dec. 9, 1997, for "Apparatus and method for Intrabody Mapping"; U.S. Pat. No. 5,454,370, issued Oct. 3, 1995, for "Mapping and Ablation Electrode Configuration"; U.S. Pat. No. 5,487,385, issued Jan. 30, 1996, for "Atrial Mapping and Ablation Catheter System"; U.S. Pat. No. 5,476,495, issued Dec. 19, 1995, for "Cardiac Mapping and Ablation Systems"; U.S. Pat. No. 5,327,889, issued Jul. 12, 1994, for "Mapping and Ablation Catheter with Individually Deployable Arms and Method"; and U.S. Pat. No. 5,263,493, issued Nov. 23, 1993, for "Deflectable Loop Electrode Array Mapping and Ablation catheter for Cardiac Chambers", each of which is incorporated herein by reference.

Another procedure facilitated by the present invention is assessing the viability of myocardial tissue before performing an invasive procedure such as angioplasty or coronary artery bypass surgery. Tissue which can be salvaged is defined as living, cells which are not contracting during cardiac systole. One method for determining tissue viability is to place a catheter having an ECG recording electrode against the endocardial surface of the heart. The presence of an ECG signal of a given magnitude indicates the presence of living cells in this region. The contraction of the heart wall at the catheter position is determined by localizing the catheter tip in real time, and noting the difference in its locations over the cardiac cycle. If little movement is noted, but electrical activity is present, the tissue may be recoverable via revascularization in this region. The cardiac electrophysiology method and system of the present invention can provide precise localization and ECG information by guaranteeing tissue contact during the cardiac cycle. Since this information needs to be collected over a large portion of the endocardial surface in the presence of anatomical impediments, magnetic distal tip control will greatly reduce the time required to complete the procedure. The system can even be set up to automatically move from point to point along the endocardial surface, collecting data at each point, and to even select its own points based upon the measurements of electrophysiological activity and motion. Finally, the MSS can return the catheter tip to a point in space with greater precision than can be expected from a mechanically controlled catheter.

Revascularization of viable myocardium is being attempted today by percutaneous myocardial revascularization (PMR) techniques, in which holes are created in the myocardial tissue to stimulate the growth of capillary vessels, which in time combine to form small arteries which feed the tissue. Drugs or genetically engineered growth factors may be applied to further stimulate the growth of vessels in the region. Using mechanical guidance to deliver these therapies results in an uncontrolled and random delivery of therapy. The MSS will allow precise delivery of therapy to regions which have been determined to contain viable myocardium.

The ability to automatically navigate also allows certain difficult and time-consuming procedures to be automated. For example, an accepted treatment of atrial flutter, is to form a line of lesions in the heart tissue to block the transmission of errant signals. This line of lesions is presently formed by manipulating the distal end of a catheter to a selected position actuating the catheter to ablate the tissue, and continuing on to form a continuous line of lesions by successively repositioning and actuating the catheter. This procedure can be greatly improved in accordance with the present invention. With the present invention, the physician can input a series of points to which the catheter tip is automatically navigated. Not only is the catheter automatically navigated to the selected lesion sites, but in accordance with this invention, proper contact between the distal end of the catheter is assured, ensuring that the lesion will be properly and completely formed. If the catheter is not in proper contact with the surface of the heart, actuation of the electrodes could form clots in the blood in the heart chamber. Rather than identify a series of point, the physician interface can simply allow the physician to identify a starting point, and ending point, and a desired resolution, and the controller can automatically position the catheter at the points along a line on the surface of the heart connecting the selected starting and ending points.

What is claimed is:

1. A method of applying a magnetic medical device to the surface of an internal body structure, the medical device having a magnetically responsive element associated with its distal end, the method comprising applying a magnetic field to the distal end of the magnetic medical device to apply a measured and controlled force between the medical device and tissue.

2. The method according to claim 1 wherein the force between the medical device and the tissue is controlled by varying at least one of the strength of the applied magnetic field and the direction of the applied magnetic field.

3. The method according to claim 1 wherein the force between the medical device and the tissue is controlled not to exceed a predetermined maximum bound.

4. The method according to claim 1 wherein the force between the medical device and the minimum is controlled to exceed the predetermined minimum bound.

5. A method of applying a magnetic medical device to the surface of an internal body structure, the medical device having a magnetically responsive element associated with its distal end, the method comprising applying a magnetic field to the distal end of the magnetic medical device to orient the distal end of the magnetic medical device generally toward the surface of the internal body structure, comparing the angle between the direction of the distal end of the magnetic medical device with the direction of the applied magnetic field; and advancing the distal end of the magnetic medical device toward the surface of the internal body structure and/or adjusting the direction of the applied magnetic field until the angle between the direction of the distal end of the magnetic medical device and the applied magnetic field indicate that the magnetic medical device is in contact with the surface of the internal body structure.

6. The method according to claim 5 wherein the distal end of the magnetic medical device is advanced toward the surface of the internal body structure until the angle between the direction of the distal end of the magnetic medical device and the applied magnetic field indicate that the magnetic medical device is in contact with the surface of the internal body structure.

7. The method according to claim 5 wherein the direction of the applied magnetic field is adjusted until the angle between the direction of the distal end of the magnetic medical device and the applied magnetic field indicate that the magnetic medical device is in contact with the surface of the internal body structure.

8. The method according to claim 5 wherein the distal end of the magnetic medical device is advanced toward the surface of the internal body structure and the direction of the applied magnetic field is adjusted until the angle between the direction of the distal end of the magnetic medical device and the applied magnetic field indicate that the magnetic medical device is in contact with the surface of the internal body structure.

9. The method according to claim 5 wherein the magnetic medical device is advanced manually.

10. The method according to claim 5 wherein the magnetic medical device is advanced automatically.

11. The method according to claim 5 wherein the magnetic medical device is applied to the surface of a moving body structure, and wherein the distal end of the magnetic medical device is advanced toward the moving surface of the internal body structure until the angle between the direction of the distal end of the magnetic medical device and the applied magnetic field indicates that the magnetic medical device is in contact with the surface of the internal body structure during its entire range of motion.

12. The method according to claim 11 wherein the magnetic medical device is advanced automatically.

13. The method according to claim 11 wherein the magnetic medical device is advanced automatically.

14. A method of applying a magnetic medical device to the surface of an internal body structure with a predetermined minimum force, the medical device having a magnetically responsive element associated with its distal end, the method comprising applying a magnetic field to the distal end of the magnetic medical device to orient the distal end of the magnetic medical device generally toward the surface of the internal body structure, comparing the angle between the direction of the distal end of the magnetic medical device with the direction of the applied magnetic field; and advancing the distal end of the magnetic medical device toward the surface of the internal body structure until the angle between the direction of the distal end of the magnetic medical device and the applied magnetic field indicate that the magnetic medical device is in contact with the surface of the internal body structure; adjusting at least one of the applied magnetic field intensity and applied magnetic field direction so that the distal end of the magnetic medical device contacts the surface of the body structure with at least the predetermined minimum force.

15. The method according to claim 14 wherein only the magnetic field direction is adjusted.

16. The method according to claim 14 wherein only the magnetic field strength is adjusted.

17. The method according to claim 14 wherein both the magnetic field direction and the magnetic field intensity are adjusted.

18. The method according to claim 14 wherein the magnetic medical device is applied to the surface of a moving body structure, and at least one of the applied magnetic field intensity and applied magnetic field direction arc adjusted so that the distal end of the magnetic medical device contacts the surface of the body structure with at least the predetermined minimum force during its entire range of motion.

19. The method according to claim 18 wherein only the magnetic field direction is adjusted.

20. The method according to claim 18 wherein only the magnetic field strength is adjusted.

21. The method according to claim 18 wherein both the magnetic field direction and the magnetic field intensity are adjusted.

22. A method of mapping the surface of an internal body structure comprising successively applying a magnetic medical device, having a magnetically responsive element associated with its distal end, to a plurality of points on the surface of the internal body structure by magnetically navigating the distal end of the magnetic medical device into contact with each of the points on the surface of the body; and determining the location of the distal end when the distal end is in contact with the surface as of the body structure as determined when the direction of the distal end of the magnetic medical device angle and the direction of the applied magnetic field exceeds a predetermined threshold.

23. The method according to claim 22 wherein the points are manually selected on an image of the structure.

24. The method according to claim 22 wherein the points are determined in a predetermined relationship to a selected point.

25. The method according to claim 22 wherein the magnetic medical device is magnetically navigated to contact a first point on the surface, successively retracted an magnetically directed into contact with the surface at one or more points by varying the magnetic field.

26. The method according to claim 22 wherein the magnetic medical device is automatically navigated to subsequent points based upon a mathematical model.

27. A method of mapping the moving surface of an internal body structure comprising successively applying a magnetic medical device, having a magnetically responsive element associated with its distal end, to a plurality of points on the moving surface of the internal body structure by magnetically navigating the distal end of the magnetic medical device into contact with each of the points on the surface of the body; and determining the location of the distal end when the distal end is in contact with the surface as of the body structure as determined when the direction of the distal end of the magnetic medical device angle and the direction of the applied magnetic field exceeds a predetermined threshold, at a plurality of points during the movement of the surface.

28. The method according to claim 27 wherein the points are manually selected on an image of the structure.

29. The method according to claim 27 wherein the points are determined in a predetermined relationship to a selected point.

30. The method according to claim 27 wherein the magnetic medical device is magnetically navigated to contact a first point on the surface, successively retracted an magnetically directed into contact with the surface at one or more points by varying the magnetic field.

31. The method according to claim 27 wherein the magnetic medical device is automatically navigated to subsequent points based upon a mathematical model.

32. A method of physiologically mapping the surface of an internal body structure comprising successively applying a magnetic medical device, having a magnetically responsive element associated with its distal end, to a plurality of points on the surface of the internal body structure by magnetically navigating the distal end of the magnetic medical device into contact with each of the points on the surface of the body; and determining the location of the distal end when the distal end is in contact with the surface as of the body structure as determined when the direction of the distal end of the magnetic medical device angle and the direction of the applied magnetic field exceeds a predetermined threshold, and measuring the physiological property at the determined location.

33. The method according to claim 32 wherein the points are manually selected on an image of the structure.

34. The method according to claim 33 wherein the points are determined in a predetermined relationship to a selected point.

35. The method according to claim 32 wherein the magnetic medical device is magnetically navigated to contact a first point on the surface, successively retracted and magnetically directed into contact with the surface at one or more points by varying the magnetic field.

36. The method according to claim 32 wherein the magnetic medical device is automatically navigated to subsequent points based upon a mathematical model.

37. The method according to claim 32 wherein the magnetic medical device is automatically navigated to subsequent points based upon the physiological data previously measured.

38. A system for making contact between a catheter and points on the surface of an internal body structure in which magnetic forces are applied;
  a source magnet for applying a magnetic field of changeable direction and strength within an operating region in a patient;
  a magnetic medical device adapted to be introduced into the operating region in the patient, having a magnet element, responsive to the magnetic field of the source magnet, associated with its distal end;
  a localization device for determining the orientation of the distal end portion of the medical device;
  a processor for comparing the direction of the distal end of the catheter and the direction of the applied magnetic field and adjusting the direction and/or strength of the magnetic field to cause the distal end of the magnetic medical device to press against the surface of the body structure with a predetermined force.

39. The system according to claim 38 further comprising a display for displaying the contact force between the magnetic medical device and the surface of the body structure.

40. A method of mapping a portion of a heart comprising the steps of:
  orienting a magnetic medical device in the heart with an externally applied magnetic field, and contacting the magnetic medical device with the surface of the heart by advancing the medical device and/or changing the direction of an externally applied magnetic field until the angle between the direction of the applied magnetic field and the direction of the medical device indicates that the medical device is in contact with the surface of the heart;
  measuring at least one physiological property of the heart at the point of contact with the magnetic medical device;
  recording the measured physiological property;
  determining the position of the distal end of the magnetic medical device; and
  creating a map of the measured physiological properties and their locations.

* * * * *